(12) United States Patent
Aksakal

(10) Patent No.: US 11,633,179 B2
(45) Date of Patent: Apr. 25, 2023

(54) RETRACTOR SYSTEM

(71) Applicant: Orhan Seyfi Aksakal, Ankara (TR)

(72) Inventor: Orhan Seyfi Aksakal, Ankara (TR)

( * ) Notice: Subject to any disclaimer, the term of this patent is extended or adjusted under 35 U.S.C. 154(b) by 0 days.

(21) Appl. No.: 16/969,199

(22) PCT Filed: Feb. 18, 2019

(86) PCT No.: PCT/TR2019/000013
§ 371 (c)(1),
(2) Date: Aug. 12, 2020

(87) PCT Pub. No.: WO2019/236027
PCT Pub. Date: Dec. 12, 2019

(65) Prior Publication Data
US 2020/0405281 A1 Dec. 31, 2020

(30) Foreign Application Priority Data

Feb. 21, 2018 (TR) .................. 2018/02480

(51) Int. Cl.
*A61B 17/02* (2006.01)
*A61B 17/42* (2006.01)

(52) U.S. Cl.
CPC ...... *A61B 17/0206* (2013.01); *A61B 17/4241* (2013.01); *A61B 2017/0212* (2013.01); *A61B 2017/4225* (2013.01)

(58) Field of Classification Search
CPC ............ A61B 17/0293; A61B 17/0206; A61B 17/0281; A61B 17/4241; A61B 2017/4216; A61B 2017/4225
See application file for complete search history.

(56) References Cited

U.S. PATENT DOCUMENTS

| | | | |
|---|---|---|---|
| 5,447,526 A * | 9/1995 | Karsdon | A61N 1/36007 607/39 |
| 5,716,327 A | 2/1998 | Warner et al. | |
| 5,769,820 A | 6/1998 | Rammler | |
| 5,947,896 A * | 9/1999 | Sherts | A61B 17/0293 600/229 |
| 6,024,697 A * | 2/2000 | Pisarik | A61B 1/32 600/224 |
| 6,030,340 A * | 2/2000 | Maffei | A61B 17/0293 600/233 |
| 6,099,468 A | 8/2000 | Santilli et al. | |
| 6,241,655 B1 * | 6/2001 | Riess | A61B 17/0206 600/37 |
| 8,974,381 B1 * | 3/2015 | Lovell | A61B 90/30 600/222 |
| 2007/0213597 A1 * | 9/2007 | Wooster | A61B 17/02 600/234 |
| 2008/0183046 A1 * | 7/2008 | Boucher | A61B 17/0206 600/232 |
| 2010/0198214 A1 * | 8/2010 | Layton, Jr. | A61B 17/42 606/213 |
| 2011/0270042 A1 * | 11/2011 | Giulianotti | A61B 17/02 211/85.13 |
| 2012/0041465 A1 * | 2/2012 | Shalon | A61B 17/0401 606/191 |
| 2016/0287224 A1 * | 10/2016 | Castro | A61B 17/0206 |

* cited by examiner

*Primary Examiner* — Nicholas J Plionis
(74) *Attorney, Agent, or Firm* — John Alumit

(57) ABSTRACT

The invention relates to an abdominal retractor system using human body parts as support points by means of extension levers, and maintains approach to the surgical region by pressing abdominal wall downwards.

17 Claims, 6 Drawing Sheets

RETRACTOR SYSTEM

TECHNICAL FIELD

The invention is related to an abdominal retractor system which uses human body parts as support by means of its extension levers.

BACKGROUND OF THE INVENTION

In existing retractor arrangements, it is not used to support another body region, such as vagina or back of the patient, to open the operating area in the abdomen or to push the abdominal wall edges toward the surgical point and facilitate the operation. In the present embodiments, a retractor draws a person from the surgical team or opens the abdominal wall only on either side or receives support from the operating table.

Technical problems aimed to be solved by the invention: It minimizes the abdominal wall factor which complicates the operation, and eliminates excessive tugging to open the surgical field. Tissue trauma and postoperative pains are minimized. Therefore, the operation time is shortened and a greater advantage is obtained with a small incision. The patient is discharged earlier from the hospital. It is pushed to the operating area by pressing the side down. This reduces the need for lateral opening. Therefore, the side of the operation can be kept smaller as the ailments and pains caused by the tension decrease.

DESCRIPTION OF THE FIGURES

The retractor system for achieving the object of the present invention is illustrated in the attached figures. These illustrations are illustrative and do not limit the purpose.

DESCRIPTION OF THE REFERENCES IN THE FIGURES

Figure 1:
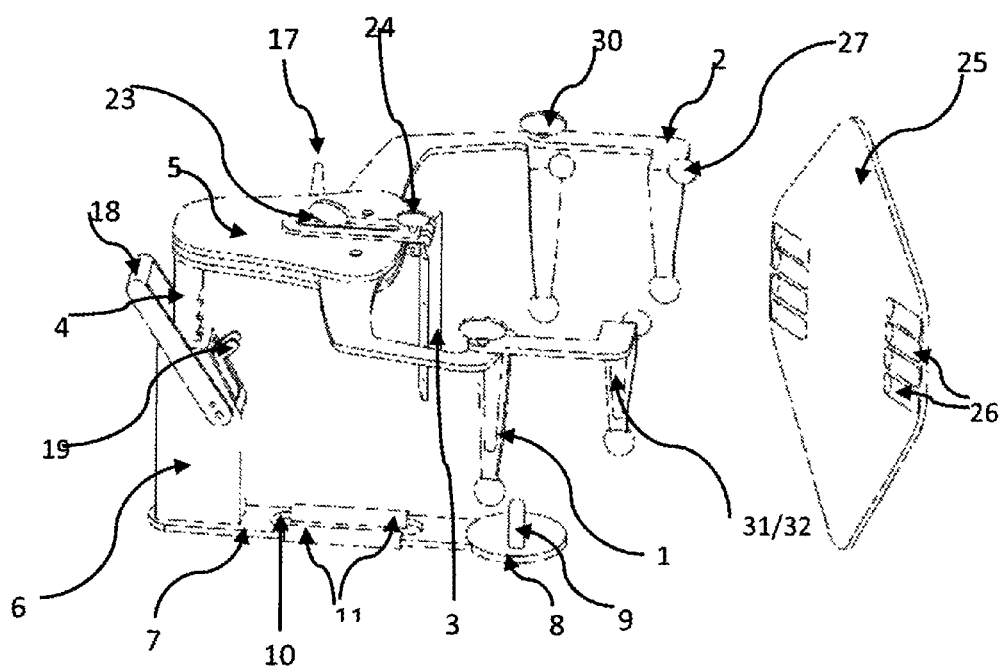
FIG. 1. The upper oblique view of the entire assembly.

1. Main retractors
2. Extension retractors
3. Front retractor
4. Main retractor block gear bar
5. Table
6. Pull-down mechanism
7. Vaginal arm with soft padded urethral window
8. Cavity for cervix uteri
9. Cervical spur/protrusion
10. Urethral opening in the vaginal arm
11. Soft pillows
12. Threaded Rod Hole
13. Threaded rod blades
14. Threaded rod channel
15. Main retractors contact gear
16. Gear locking mechanism to prevent closure of main retractors
17. Anti-lock mechanism lever
18. Pull-down lever
19. Stop handle
20. Stop handle pressure spring
21. Pull handle
22. Pull handle spring
23. Front retractor forward-backward position fixing screw
24. Front retractor end section position fixing screw
25. Bowel retractor
26. Stop channels
27. Stop overhangs
28. Main retractor down-press zone
29. Main retractor round tip
30. Extension retractor clamping screw
31. Pressure/strain sensors
32. Power generator tips
33. Ball nut
34. Screw
35. Horizontal axis of extension retractors

DESCRIPTION OF THE INVENTION

Figure 2:
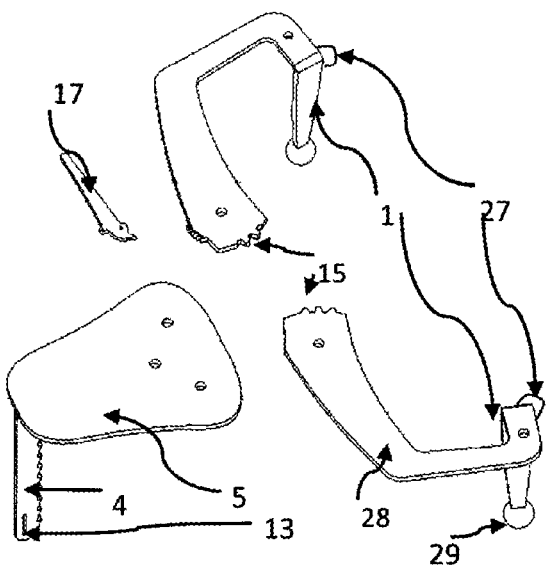
FIG. 2. Top and bottom oblique views of the main retractors, table and the closing arm.
Figure 3:
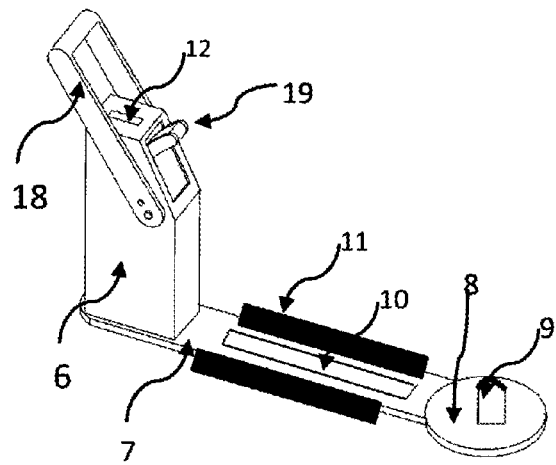
FIG. 3. Vaginal arm and mechanism box upper oblique view.
Figure 6:
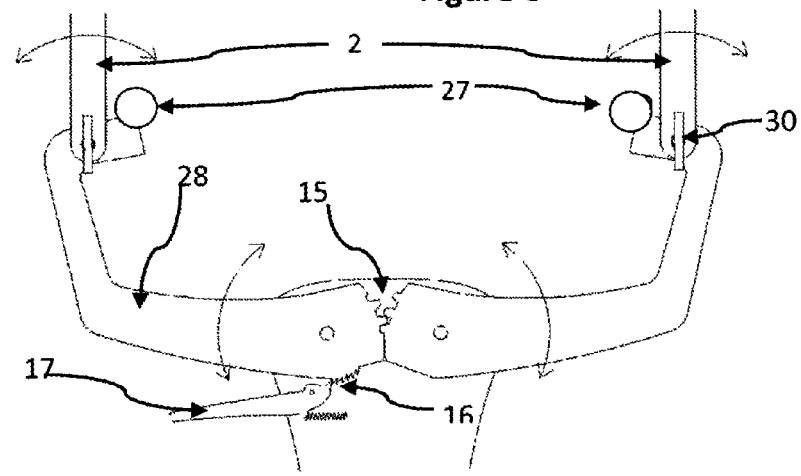
FIG. 6. The mode of movement of the main retractors and extension retractors and the structure of the release arm.
Figure 7:
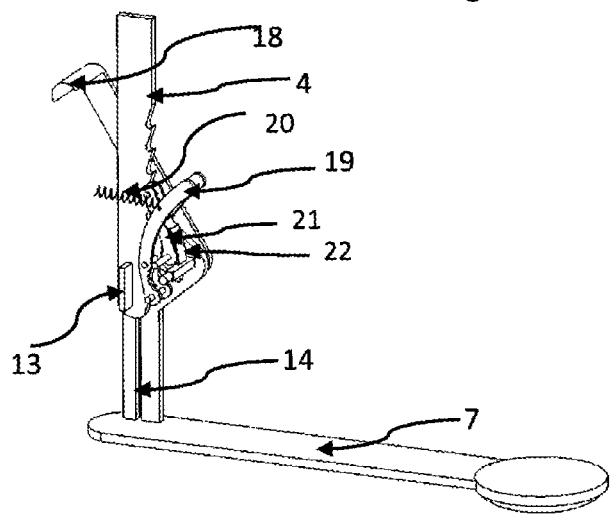
FIG. 7. Mechanism box interior details—springs and arms—oblique view.
Figure 9:
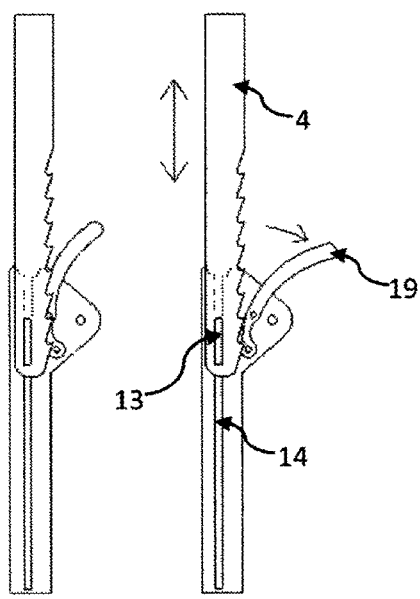
FIG. 9. The function of releasing the arm and retractors from each other of the stop arm—side view.
Figure 10:
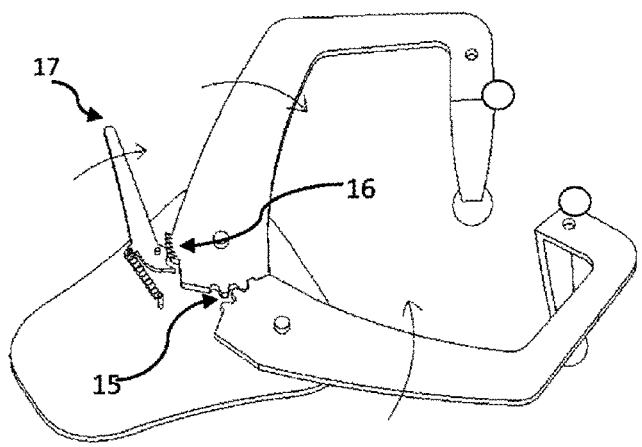
FIG. 10. It is the upper oblique view of the main retractor closing lever operation and the relation of the main retractors.
Figure 11:
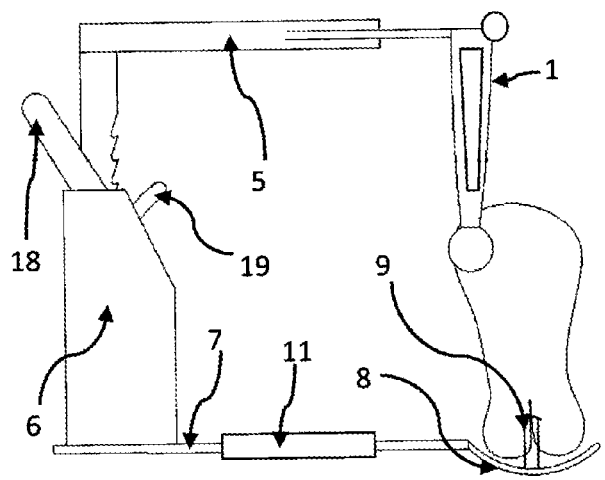
FIG. 11. When the system is applied to the patient, its relation with the organ (cervix)—side view.

In normal position; the main retractor (1), extension retractors (2), the front retractor (3), the rod and the main retractor block gear bar (4) (FIGS. 1,2, 6), which consists of a table (5) that holds them all together, and the pull-down mechanism (6), the pitted vaginal arm (7) (FIGS. 3, 7, 11, 12) is separated from one another. The vaginal arm (7) is inserted into the chamber and pushed forward. There's a cervix here. The vaginal arm (7) slides underneath it into the cavity (8) at the end of the cervix (FIG. 11). The protrusion at the end (9) also forms an additional fixation by entering the cervical canal (FIG. 11). There is an opening (10), such as a urethra opening, on the vaginal arm (7) to prevent the urine tube from being crushed (FIGS. 1, 3, 7). On both sides of this opening there are soft pillows (11) so as not to damage the container wall. Then, the gear bar (4) of the main retractor block in the closed position is inserted into the hole (12) in the pull-down mechanism connected to the vaginal arm (FIG. 1). The toothed rod blade (13), entering here, enter the channel (14) (FIGS. 7, 8, 9) through which they move up and down. It is pushed as far as it can be pushed. Thus, the vaginal arm (7), which carries the main retractor block and the mechanism, is pushed against one another and the main retractors are opened to one side in connection to the muscles on both sides. The main retractors (1) are associated with each other by means of a gear (15) and are opened to the same degree (FIG. 6). Closing of the main retractors is prevented by a gear locking mechanism (16) (FIG. 6). This mechanism has an anti-lock mechanism lever (17). When this lever is pressed, the main retractors (1) can immediately be moved to their original positions (FIG. 10).

Figure 8:
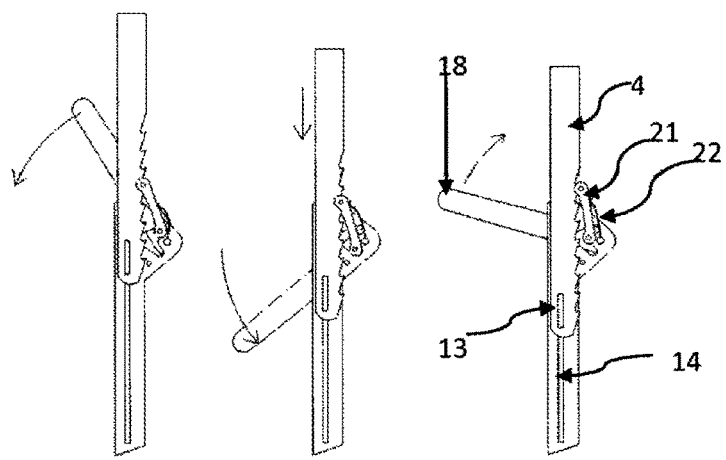
FIG. 8. The operating system of the pull-down lever—side view

If the main movement of the main retractors towards the vaginal arm (7) is desired, 25 the pull-down lever (18) of the pull-down mechanism is pressed down to the end (FIG. 8). The stop handle (19) prevents from escaping upwards again. This stop handle (19) is always held in pressed form with a first spring (20) in order to prevent back-flow. Each full downward movement of the pull-down lever (18) pulls down a shaft-driven pull handle (21) in the pull-down mechanism housing. The shaft at the end of the pull handle (21) is seated on a tooth on the rod blade (13) and is pressed by means of a second spring (22). The pull handle (21), seated on a tooth, lowers main retractors (1) and the extension retractors connected to thereof by one tooth (FIG. 8). The retractors will be lowered as much as needed by means of required motion. In case of a need for removal of the retractor assembly from the vaginal arm, the stop handle (19) is pressed backwards (FIG. 9). A long screw mounted on the arm (7) can be adapted by means of a ball nut mounted on the plate (5) instead of the mechanism (6) and the main retractor block gear bar (4) to approach the arm (7).

Figure 5:
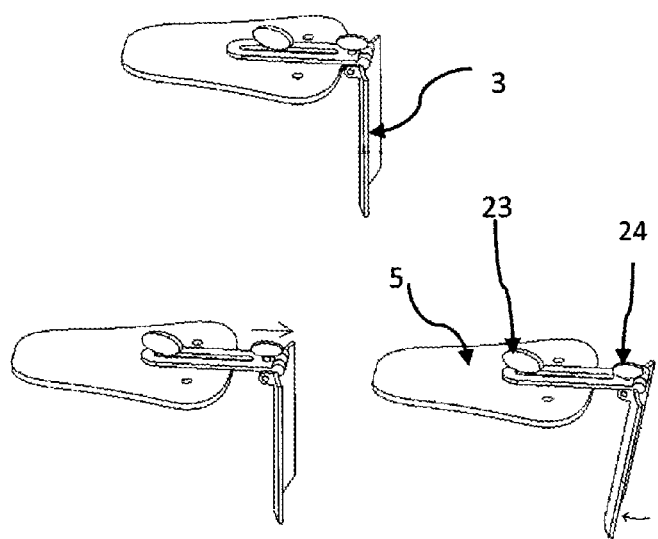
FIG. 5. Oblique view of the front (bladder) retractor and movements.

There is a front retractor (3), which can be adjusted to the pubic bone, namely the forward-backward position fixation screw (23), in the region close to the bladder and the angle of the tip to the screw (24) (FIG. 5).

Figure 4:
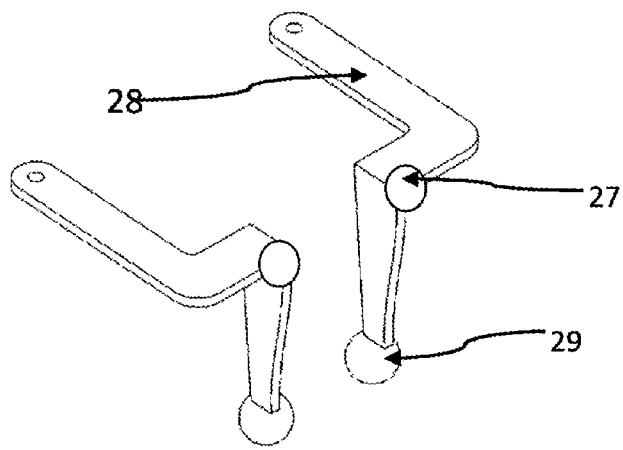
FIG. 4. The upper oblique view of the extension retractors.
Figure 13:
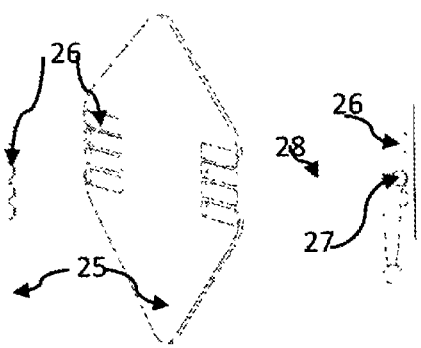
FIG. 13. Relation of the intestine retractor and stop protrusions—side and oblique view.

There are also extension retractors (2), which can be adjusted both downwards and sideways for wide abdominal operations extending upwards (FIGS. 1, 4, 6). To keep the bowels away from the surgical site, there is a compatible bowel retractor (25) (FIGS. 1, 13). On the side of this retractor facing the main retractor system, there are stop channels (26) on both sides. The stop overhangs (27) at the end of the retractors enter those channels at the appropriate level. Since the channels are transversely long towards sides, they adapt to lateral opening of the retractor and the bowel retractor (25) can maintain its position without sliding upwards (FIG. 13).

Figure 12:
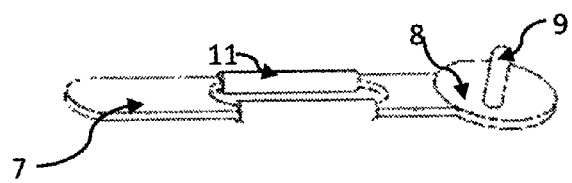
FIG. 12. Upper oblique view of the urethral window supports silicone soft cervical fixation bar and the lower oblique view of the sensors.
Figure 12:
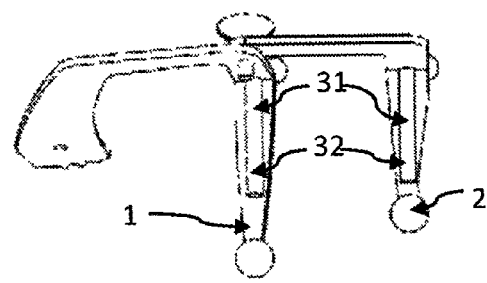

The body of the main retractors (1) and extension retractors (2) is wide and on the horizontal axis (35). Thus, it can easily lower the side abdominal walls downwards (FIGS. 1, 2, 4, 6, 10) and open the wound edges sideways with a vertical extension (FIGS. 1, 2, 4, 10, 11, 12, 14). The opening ends (29) are round and smooth so as not to damage the organs (FIGS. 1, 2, 4, 11). After the extension retractors are attached to the main retractor, the screw (30) is fixed by tightening (FIGS. 1, 6, 12).

Outside the retractors (1, 2) namely, on the muscle contacting side of the vertical part which serves to open the wound to the sideways, there are pressure sensors (31) (FIGS. 1, 11, 12). They give notice of loosening of the tissue by giving warning of the tissue being squeezed and damaged thus, tissue is protected from being crushed. Furthermore, in the same sensor area, there are generators (32) that send special electric currents to loosen the abrupt muscle contractions that occur when the dose of the anesthetic drug decreases (FIGS. 1, 11, 12).

Figure 14:
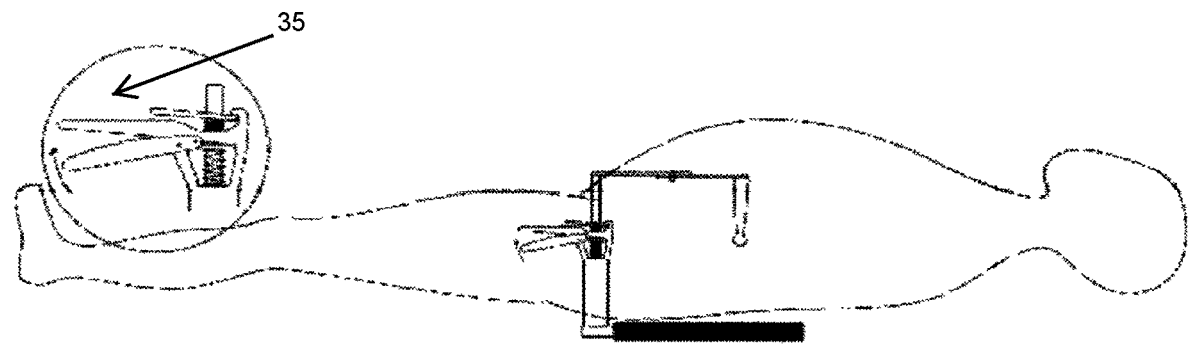
FIG. 14. The application of the arm to the patient for fat patient and the appearance of a clamping system (ratchet bar clamp).
Figure 15:
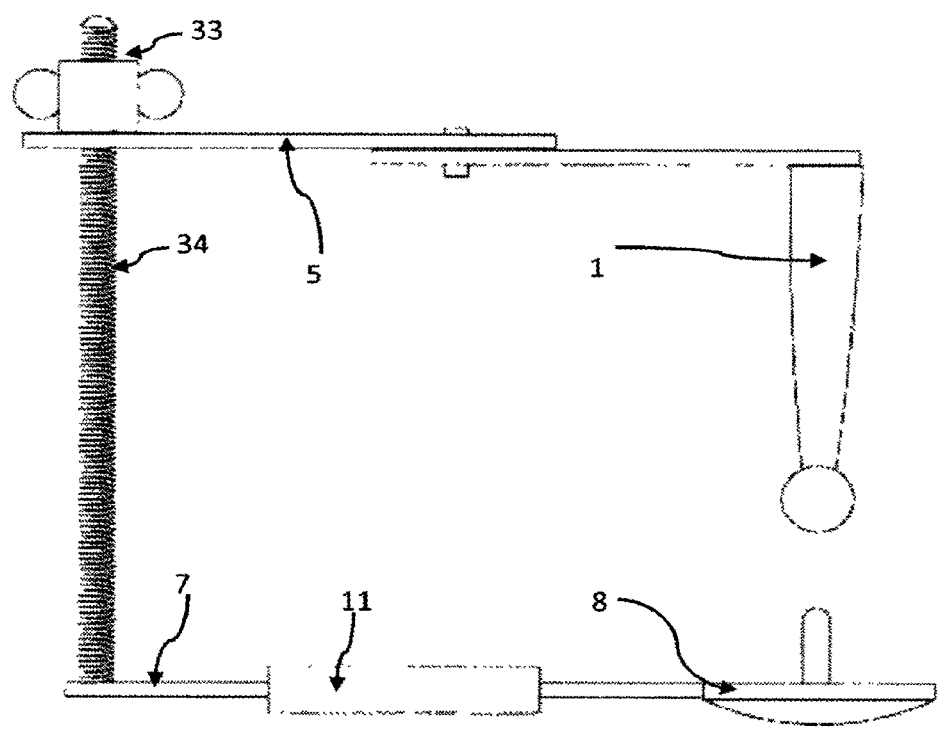
FIG. 15. Side view of the approach with using ball nut and screw instead of threaded arm and mechanism.

For fat patients, the support of the current mechanism (6) and the arm (7) from the vagina may not be sufficient. In this case, instead of the mechanism (6), one of the commercially available clamping systems will be adapted and the support will be taken from the patient's back region, covered with a soft layer but with a wider and longer arm (7) (FIG. 14).

INDUSTRIAL APPLICATION OF THE INVENTION

The retractor system which serves to the above described purposes, can be produced, and used in the corresponding branch of the industry, and has a structure applicable to the medical sector.

The invention claimed is:
1. A retractor system, comprising
a main retractor block;
a pull-down mechanism (6) with a housing; and
a vaginal arm with a soft padded urethral window (7),
wherein said vaginal arm carries the main retractor block and pull-down mechanism and
wherein said main retractor block comprises main retractors (1) connected to extension retractors (2) at one end and to a table (5) at another end, a front retractor (3) connected to the table (5), and a main retractor block gear bar (4) disposed perpendicularly to the table and attached thereto.

2. The retractor system according to claim 1, further comprising a cervical spur (9) at an end of the vaginal arm (7), wherein the cervical spur is configured to enter into a cervical canal of a patient to maintain an additional fixation when the vaginal arm (7) slides underneath the cervix uteri of the patient into a cavity.

3. The retractor system according to claim 2, wherein the vaginal arm (7) has a urethral opening (10) to prevent the urine tube of the patient from being crushed.

4. The retractor system according to claim 3, wherein soft pillows (11) are available at both sides of the urethral opening (10) for protecting the abdominal wall of the patient.

5. The retractor system according to claim 1, wherein the main retractor block gear bar (4) is provided with a toothed rod blade (13) that is inserted into a hole (12) of the pull-down mechanism, said hole leading to a channel (14), where said toothed rod blade (13) is configured to move up and down, and wherein said downward movement causes the main retractors to open.

6. The retractor system according to claim 5, wherein the main retractors (1) have a contact gear (15) for maintaining a same degree of opening of the main retractors.

7. The retractor system according to claim 6, wherein the main retractors (1) include a gear locking mechanism (16) to prevent closure of said main retractors.

8. The retractor system according to claim 7, wherein the gear locking mechanism (16) has an anti-lock mechanism lever (17) for bringing the main retractors (1) back to their original positions.

9. The retractor system according to claim 8, the pull-down mechanism comprises a lever (18) to lower the main retractors to a lowered position closer to the vaginal arm, when desired during an operation, and further comprises a stop handle (19) anchored by a first spring (20) to maintain the main retractors in said lowered position.

10. The retractor system according to claim 9, wherein the lever (18) includes a shaft-driven pull handle (21) whose shaft is pressed against the teeth of the toothed rod blade (13) by a second spring (22) so that the shaft-driven handle (21) is pulled downward along each tooth of the toothed rod blade (13) with each downward movement of the lever (18).

11. The retractor system according to claim 1, wherein proximity of the front retractor (3) to the pubic bone of a patient can be adjusted by a fixation screw (23).

12. The retractor system according to claim 1, further comprising a bowel retractor (25) to keep the bowels of a patient away from the surgery site.

13. The retractor system according to claim 12, wherein the bowel retractor (25) comprises stopping channels (26) on a side facing the main retractors (1) and the main retractors (1) further comprise stop overhangs (27) that enter the stopping channels (26) in order to maintain the position of the bowel retractor (25) and to prevent said bowel retractor from sliding upwards.

14. The retractor system according to claim 12, wherein the bodies of the main retractors (1) and extension retractors (2) open outwardly on a horizontal axis (35) and wherein the extension retractors furthermore extend vertically, further comprising round opening ends (29) which are disposed at distal ends of the extension retractors so as to open wound edges sideways and lower the sides of abdominal walls.

15. The retractor system according to claim 14, wherein a pressing screw (30) fixes the extension retractors (2) to respective main retractors.

16. The retractor system according to claim 14, wherein said system comprises pressure sensors (31) disposed on vertical sides of the main retractors and the extension retractors facing the muscle tissue of a patient.

17. The retractor system according to claim 16, wherein said system further comprises generators (32) within the vicinity of the pressure sensors (31) that send electrical currents to loosen muscle contractions resulting when anesthetic drug doses decrease.

\* \* \* \* \*